United States Patent
Itoh et al.

(10) Patent No.: US 7,874,211 B2
(45) Date of Patent: Jan. 25, 2011

(54) MEASURING METHOD AND MEASURING DEVICE USING QUARTZ OSCILLATOR

(75) Inventors: Atsushi Itoh, Kanagawa (JP); Motoko Ichihashi, Kanagawa (JP)

(73) Assignee: ULVAC, Inc., Chigasaki-Shi (JP)

( * ) Notice: Subject to any disclaimer, the term of this patent is extended or adjusted under 35 U.S.C. 154(b) by 148 days.

(21) Appl. No.: 11/988,029

(22) PCT Filed: Jun. 1, 2006

(86) PCT No.: PCT/JP2006/310974

§ 371 (c)(1),
(2), (4) Date: Dec. 28, 2007

(87) PCT Pub. No.: WO2007/004376

PCT Pub. Date: Jan. 11, 2007

(65) Prior Publication Data

US 2009/0038859 A1 Feb. 12, 2009

(30) Foreign Application Priority Data

Jun. 30, 2005 (JP) .............................. 2005-192612

(51) Int. Cl.
*G01N 5/02* (2006.01)
(52) U.S. Cl. .................. 73/579; 73/580; 177/210 FP; 310/312; 422/68.1; 435/287.1; 436/501
(58) Field of Classification Search ........... 177/210 FP; 73/580, 579; 310/312; 435/287.1; 422/68.1; 436/501

See application file for complete search history.

(56) References Cited

U.S. PATENT DOCUMENTS

| 5,552,274 | A | * | 9/1996 | Oyama et al. | ............... | 435/6 |
| 5,814,525 | A | * | 9/1998 | Renschler et al. | ......... | 436/524 |
| 5,869,763 | A | * | 2/1999 | Vig et al. | ................... | 73/580 |

FOREIGN PATENT DOCUMENTS

| JP | 07-055860 | A | * | 3/1995 |
| JP | 2001-304945 | | | 10/2001 |
| JP | 2003-315235 | | | 11/2003 |
| JP | 2004-184256 | | | 7/2004 |
| JP | 2004-325257 | | | 11/2004 |
| JP | 2005-98866 | | | 4/2005 |
| JP | 2006-52996 | | | 2/2006 |
| JP | 2007-071722 | A | * | 3/2007 |

\* cited by examiner

*Primary Examiner*—Randy W Gibson
(74) *Attorney, Agent, or Firm*—Kratz, Quintos & Hanson, LLP

(57) ABSTRACT

An object of the present invention is that any of mass load, viscous load and viscoelasticity load is measured separately from other load whereby properties of the substance to be measured are able to be measured correctly.

The characteristic feature of the present invention is that, in a method where property of a substance contacting to a quartz oscillator equipped with electrodes on both sides of a quartz plate is measured on the basis of the changes in frequency of the above quartz oscillator, the property of the above substance is measured using at least two frequencies among the n-th overtone mode frequency ($n=1, 3, 5, \ldots$ ($n=2k+1$)) of quartz oscillator when voltage is applied between the above electrodes and using frequencies $F_1$, $F_2$ ($F_1 < F_2$) giving one half of the maximum value of conductance near the resonant point by each frequency.

3 Claims, 4 Drawing Sheets

Note: avidin (1), b-DNA (1) and c-DNA (1) are changes in frequency by fundamental mode frequency and avidin (3), b-DNA (3) and c-DNA (3) are changes in frequency by third overtone mode frequency.

MEASURING METHOD AND MEASURING DEVICE USING QUARTZ OSCILLATOR

TECHNICAL FIELD

The present invention relates to a measuring method and a measuring device using a quartz oscillator.

BACKGROUND ART

QCM (quartz crystal microbalance) has been widely used for the measurement, etc. utilizing interaction and antigen-antibody reaction of biomaterials such as DNA and protein.

However, in the case of the conventional QCM, changes in resonance frequency $F_s$ are measured whereby a binding amount of a substance to a quartz oscillator is measured but, since the resonance frequency may be affected by changes in viscosity and changes in viscoelasticity of the substance in addition to by mass load, those three elements have not been able to be measured separately.

DISCLOSURE OF THE INVENTION

Problems that the Invention is to Solve

Under such circumstances, an object of the present invention is that any of mass load, viscous load and viscoelasticity load is measured separately from other loads whereby properties of the substance to be measured are able to be measured correctly.

Means for Solving the Problems

In order to solve the above problems, the present inventor has obtained the following finding as a result of intensive studies.

From Martin's transmission theory (V. E. Granstaff, S. J. Martin, *J. Appl. Phys.*, 1994, 75, 1319), changes in inductance Z when a substance having viscoelasticity is adhered to a quartz oscillator in a liquid is expressed by the formula (1). In the formula, $\omega$ is angular frequency, $\eta$ is viscosity of the liquid, $\rho$ is density of the liquid, h is film thickness, G is shear modulus, G' is storage elasticity and G" is loss elasticity.

[Formula 1]
$$Z = (\omega \rho_2 \mu_2 / 2)^{1/2}(1+j) + j\omega\rho_1 h_1 + \frac{(G' - jG'')}{|G|^2}\omega^2 \rho_2 \eta_2 h_1 \qquad (1)$$

From the formula (1), changes in the resonance frequency $F_s$ are as shown by the formula (2).

[Formula 2]
$$\Delta F_S = \text{Im}(Z) = -(\omega \rho_2 \eta_2 / 2)^{1/2} - \omega \rho_1 h_1 + \frac{(G'')}{|G|^2}\omega^2 \rho_2 \eta_2 h_1 \qquad (2)$$

When the conductance by which the above resonance frequency $F_s$ is resulted is G, the frequency where the conductance is one half ($\frac{1}{2}$ G) thereof is $F_1$, $F_2$ ($F_1 < F_2$) (FIG. 1). Changing amount of this one-half frequency $(F_1 - F_2)/2$ is expressed by the formula (3).

[Formula 3]
$$\Delta(F_1 - F_2)/2 = \text{Re}(Z) = -(\omega \rho_2 \eta_2 / 2)^{1/2} + \frac{(G')}{|G|^2}\omega^2 \rho_2 \eta_2 h_1 \qquad (3)$$

On the other hand, changes in another frequency $F_2$ are expressed by the formula (4) in view of the relation of $F_s = (F_1 + F_2)/2$.

[Formula 4]
$$\Delta F_2 = -\omega\rho_1 h_1 + \frac{(G' + G')}{|G|^2}\omega^2 \rho_2 \eta_2 h_1 \qquad (4)$$

When $G = G' + iG'' = \mu + i\omega\eta$ which is a Voight model being a model of viscoelasticity of film is applied to G' and G" in the formula, the formula (4) and the formula (3) become as follows.

[Formula 5]
$$\Delta F_2 = -\omega\rho_1 h_1 + \frac{(\mu_1 + \omega\eta_1)}{(\mu_1^2 + \omega^2\eta_1^2)}\omega^2 \rho_2 \eta_2 h_1 \qquad (5)$$

Mass Load Viscoelasticity Term 1

[Formula 6]
$$\Delta(F_1 - F_2)/2 = -(\rho_2 \eta_2 \omega / 2)^{1/2} - \frac{\mu_1}{(\mu_1^2 + \omega^2\eta_1^2)}\omega^2 \rho_2 \eta_2 h_1 \qquad (6)$$

Viscous load Viscoelasticity Term 2

Here, when expansion is done to an overtone of n-th (in which n=3, 5, ...) (when $\omega$ is a fundamental mode frequency, $N\omega$ is angular frequency of n-th overtone mode frequency) with a proviso that $$\omega\eta_1 = C\mu_1 \qquad \text{[Formula 7]}$$

(in which C is a variable), the formulae (5) and (6) become as follows. Incidentally, $F_{1N}$ and $F_{2N}$ are frequencies ($F_1$ and $F_2$) when resonance is done with n-th overtone mode frequency.

[Formula 7]
$$\Delta F_{2N} = -N\omega\rho_1 h_1 + \frac{(1 + CN)}{\mu_1(1 + C^2N^2)}N^2\omega^2 \rho_2 \eta_2 h_1 \qquad (7)$$

[Formula 8]
$$\Delta(F_{1N} - F_{2N})/2 = -(\rho_2 \eta_2 N\omega / 2)^{1/2} - \frac{1}{\mu_1(1 + C^2N^2)}N^2\omega^2 \rho_2 \eta_2 h_1 \qquad (8)$$

Changes in frequency of overtone by mass load shows the changes in n-th overtone mode frequency of changing amount of frequency by mass load of fundamental mode frequency and, therefore, when the difference between the changing amount ($\Delta F_{21}$) of mass load by fundamental mode frequency and the changing amount ($\Delta F_{23}/3$) of mass load by third overtone mode frequency or, in other words, ($\Delta F_{21} - \Delta F_{23}/3$) is determined, that is as shown by the formula (9).

Further, since changes in frequency of overtone by viscous load shows the change of $\sqrt{n}$-times of changing amount of fundamental mode frequency by viscous load, when the difference in changing amount of frequency between fundamental mode frequency and third overtone mode frequency ($\Delta(F_1 - F_2)/2$) or, in other words, $((F_{11} - F_{21})/2 - ((F_{13} - F_{23})/2\sqrt{3})$ is determined, that is as shown by the formula (10).

[Formula 9]
$$\Delta F_{21} - \Delta F_{23}/3 = \left\{ \frac{(1+C)}{(1+C^2)} - \frac{3(1+3C)}{(1+9C^2)} \right\} \frac{\omega^2 \rho_2 \eta_2 h_1}{\mu_1} \qquad (9)$$

-continued

[Formula 10]

$$\Delta(F_{11} - F_{21})/2 - \Delta(F_{13} - F_{23})/2\sqrt{3} = \left\{ -\frac{1}{(1+C^2)} + \frac{3\sqrt{3}}{(1+9C^2)} \right\} \frac{\omega^2 \rho_2 \eta_2 h_1}{\mu_1} \quad (10)$$

When the measuring system solely comprises the mass load in the formula (9), the value of the right side is theoretically 0 while, when a viscoelasticity term 1 is contained, the value of the right side is the value of the viscoelasticity term 1.

It is also the same in the formula (10) that, when the measuring system solely comprises the viscous load therein, the value of the right side is theoretically 0 while, when a viscoelasticity term 2 is contained, the value of the right side is the value of the viscoelasticity term 2.

Here, since the left sides of the formulae (9) and (10) are measured values, (9)/(10) is a formula solely comprising a variable C whereby C is able to be determined.

When C is determined, the term of

[Formula 11]

$$\frac{\omega^2 \rho_2 \eta_2 h_1}{\mu_1}$$

is able to be resulted from the formula (9), the mass load term of the formula (7) is able to be determined and, when it is substituted for the formula (5), the viscoelasticity term 1 is also able to be determined. Similarly, the viscoelasticity load term of the formula (8) is also able to be determined and, when the value is substituted for the formula (6), the viscoelasticity term 2 is also able to be determined. Accordingly, the viscoelasticity term 1 and mass load of the formula (5) are able to be obtained. Similarly, the viscous load and viscoelasticity term 2 of the formula (6) are also able to be determined.

As such, separation of mass load, viscous load, viscoelasticity term 1 and viscoelasticity term 2 were performed by the fundamental mode frequency and the third overtone mode frequency and, as shown in FIG. 2, a combination of at least two of the n-th overtone mode frequency (n=1, 3, 5, ... (n=2 k+1)) is able to be used whereby measurement is able to be conducted by, for example, changing amount of frequency of third overtone mode frequency and fifth overtone mode frequency and, furthermore, by changing amount of frequency in plural combinations such as that of fundamental mode frequency and fifth overtone mode frequency and that of third overtone mode frequency and seventh overtone mode frequency. Incidentally, in measuring the changing amount of frequency in plural combinations, the mean value of changing amounts of frequency obtained in each combination is determined whereby it is possible to make the error in each value little. In the case of three or more combinations, it is also possible to use a least-squares method.

With regard to a model for viscoelasticity, although a Voight model was used in this example, it is also possible to apply a Maxwell model $G=G'+iG''=\mu+i\eta$ and other models.

On the basis of the above finding, the measuring method according to the present invention of first embodiment is that a method where property of a substance contacting to a quartz oscillator equipped with electrodes on both sides of the quartz plate is measured on the basis of the variation in frequency of the above quartz oscillator, characterized in that, the property of the above substance is measured using at least two frequencies among the n-th overtone mode frequency (n=1, 3, 5, ... (n=2 k+1)) of the quartz oscillator when voltage is applied between the above electrodes and using frequencies $F_1$, $F_2$ ($F_1<F_2$) giving one half of the maximum value of conductance near the resonant point by each frequency.

The present invention of second embodiment is that, its characteristic feature is that, in the measuring method mentioned in first embodiment, any of mass load, viscous load and viscoelasticity load of the substance is measured separately from other load by the difference in the changing amount of $F_2$ between the above frequencies ($\Delta F_2$) and the difference in one half of the difference in $F_1$ and $F_2$ among the above frequencies ($\Delta(F_1-F_2)/2$).

The measuring device according to the present invention of third embodiment is that, it is a measuring device using the measuring method mentioned in second embodiment and its characteristic feature is that the difference in the changing amount of $F_2$ between each of the above frequencies ($\Delta F_2$) and the difference of each one half of the difference in $F_1$ and $F_2$ among the above frequencies ($\Delta(F_1-F_2)/2$) is expressed by a graph.

ADVANTAGES OF THE INVENTION

It is now possible in accordance with the present invention that, in the measurement using a quartz oscillator, at least one of mass load, viscous load and viscoelasticity load of a substance which is an object for the measurement is able to be measured separately from other loads whereby correct measure of the substance to be measured is able to be conducted.

BEST MODE FOR CARRYING OUT THE INVENTION

In the present invention, at least two frequencies among n-th overtone mode frequency (n=1, 3, 5, ... (2 k+1)) are used. Incidentally, resonance frequency by the n-th overtone mode frequency also includes the frequency near resonance frequency of the n-th overtone mode frequency and, for example, scanning of a range of about ±500 kHz is also included.

In the measurement of changes in frequency, there is used a half-value frequency $F_1$, $F_2$ ($F_1<F_2$) giving a half-value conductance in a size of one half of conductance where an oscillator is in a series resonance state.

Figure 1:
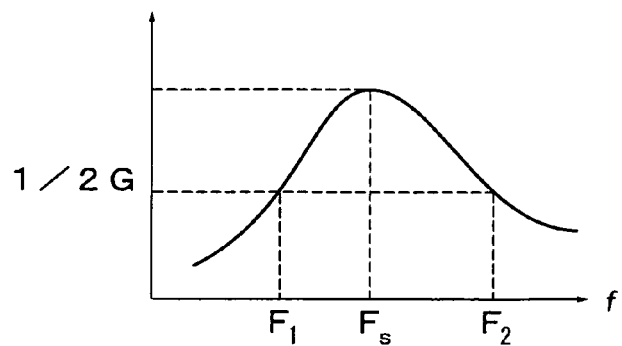
FIG. 1 is a graph which shows the relation between resonance frequency and conductance.
Figure 2:
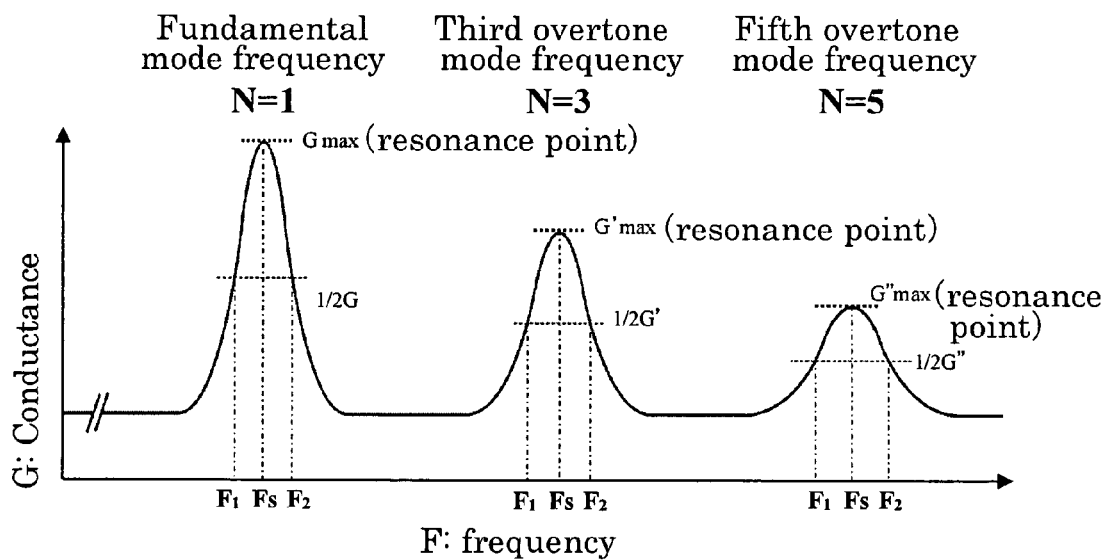
FIG. 2 is a graph which shows the relation between fundamental mode frequency and n-th overtone mode frequency.

EXPLANATION OF NUMERAL REFERENCES 1 biosensor device
2 sensor part
3 network analyzer
4 computer
5 cable
6 cable
7 quartz oscillator
8 crystal plate in circular shape
9a the first gold electrode
10a the second gold electrode
11 resin cover
12 reacting material
13 signal supplying circuit
14 measuring circuit
15 cell As hereunder, one of the embodiments of the present invention will be illustrated by referring to the drawings. Incidentally, the present invention is not limited to the embodiments as such.

Figure 3:
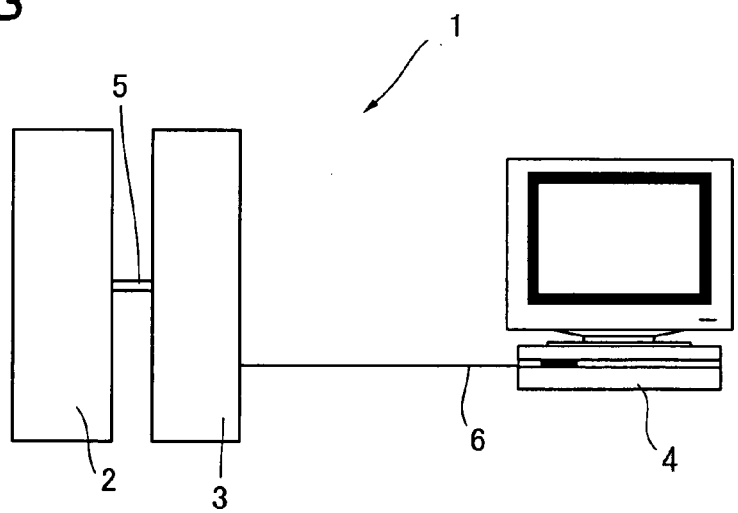
FIG. 3 is an illustrative drawing of a biosensor device which is one of the embodiments of the present invention.

In FIG. 3, the numerical reference 1 shows a biosensor device which is one of the embodiments of the present invention.

This biosensor device 1 has a sensor part 2, a network analyzer 3 and a computer 4. Each of the area between the sensor part 2 and the network analyzer 3 and the area between the network analyzer 3 and the computer 4 is respectively connected by the cables 5, 6. The sensor part 2 is equipped with a quartz oscillator.

Figure 4A:
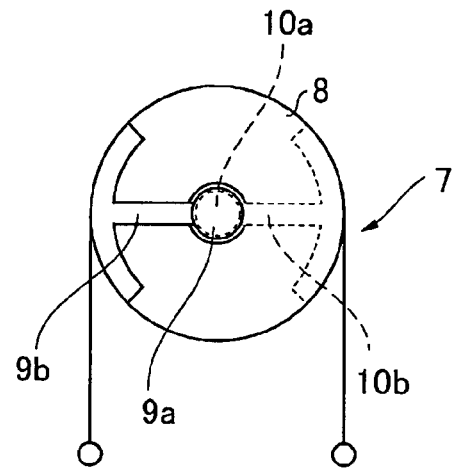
FIG. 4 is a plane view (a) and cross-sectional view (b) of a quartz oscillator of said device.
Figure 4B:
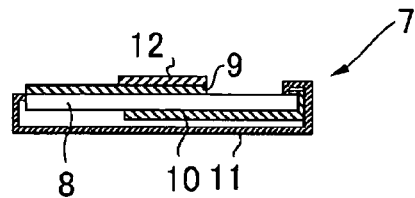

As shown in FIGS. 4(a) and (b) for its plane view and cross-sectional view, the quartz oscillator equipped in the sensor part 2 is equipped with the first gold electrode 9a and the second gold electrode 10a on the surface side and the back side, respectively, of a crystal plate 8 made of quartz in a circular shape. The gold electrodes 9a, 10a shown in the drawing are constituted in a circular shape and leading wires 9a, 10b are connected thereto, respectively. As shown in FIG. 4 (b), the second gold electrode 10a on the back side is covered by a resin cover 11 whereby it is constituted in such a manner that, even in a state where the quartz oscillator 7 is placed in a solution, the second gold electrode 10a on the back side is not exposed to the solution and oscillation is still possible. On the other hand, the surface of the first gold electrode 9a on the surface side is equipped with a reaction material 12 which reacts with a specific component so as to adsorb said component and it contacts to the sample solution upon measurement.

Figure 5:
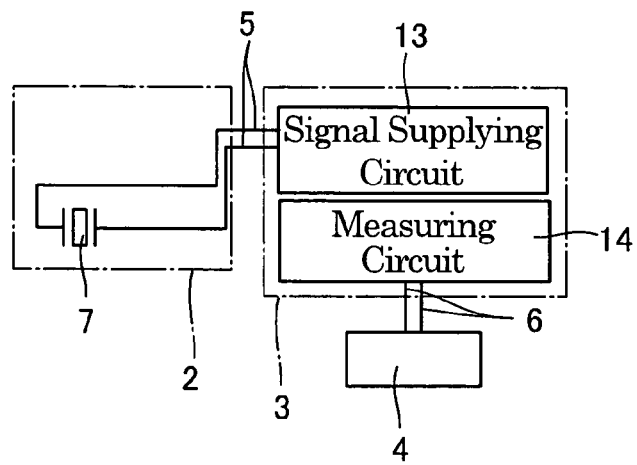
FIG. 5 is an illustrative drawing of constitution of said device.

As shown in FIG. 5, the network analyzer 3 has a signal supplying circuit 13 and a measuring circuit 14.

The signal supplying circuit 13 is constituted in such a manner that input signal of alternating current is able to be outputted together with changing the frequency.

The measuring circuit 14 is constituted in such a manner that, on the basis of output signal of the quartz oscillator 7 and input signal outputted from the signal supplying circuit 13, electrical characteristics such as phase and resonance frequency of the quartz oscillator 7 are able to be measured and outputted to the computer 4.

The computer 4 is constituted in such a manner that, on the basis of the measured electric characteristics such as frequency characteristic of the quartz oscillator 7, reaction rate, etc. of the component in the sample solution are able to be determined whereby analysis of the component is able to be done.

A procedure for the analysis of reaction state of the specific component in the sample solution such as blood with a reaction material 12 located on the surface of the quartz oscillator 7 by the biosensor device 1 having the above-mentioned constitution will now be illustrated as hereunder.

Figure 6:
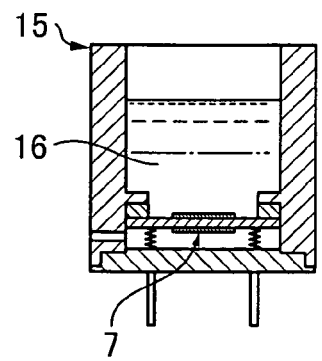
FIG. 6 is an illustrative drawing of the cell of the biosensor device.

Firstly, as shown in FIG. 6, a sample solution 8 is charged into a cylindrical cell 15 having a quartz oscillator 7 on the bottom, the network analyzer 3 is driven under the state where the quartz oscillator 7 is dipped in the sample solution 8 and control signal is outputted from the computer 4. On the basis of the outputted control signal, the input signal outputted from the signal supplying circuit 13 is outputted to the sensor part 2 via the cable 5.

When the input signal is supplied from the signal supplying circuit 13 to the quartz oscillator 7, the quartz oscillator 7 to which the input signal is supplied outputs the output signal corresponding to the input signal. As shown in FIG. 5, the output signal is outputted to the network analyzer 3 via the cable 5 and is inputted to the measuring circuit 14 in the network analyzer 3. Then the measuring circuit 14 detects the signal intensity (corresponding to the amplitude of oscillated frequency in this case) of the output signal of the quartz oscillator 7 to which the input signal is supplied.

The above signal supplying circuit 13 changes the frequency of the input signal within a predetermined frequency range and the measuring circuit 14 detects the signal intensity of the output signal whenever the frequency of the input signal changes. As a result, the relation between the frequency of the input signal and the signal intensity of the output signal is determined.

As such, the measuring circuit 14 measures the resonance frequency of the quartz oscillator 7 and the resulting resonance frequency of the quartz oscillator 7 is outputted to the computer 4 via the cable 6. After a predetermined period of time elapses, the computer 4 stops the supply of the signal.

In this embodiment, the above measurement is firstly carried out by a fundamental mode frequency of the quartz oscillator 7 and the resonance frequency by the fundamental mode frequency is determined. On the basis of the measured resonance frequency, the same measurement as in the already-mentioned measurement using the fundamental mode frequency is conducted using the n-th overtone resonance frequency.

Measurement of at least any of mass load, viscoelasticity load and viscous load which are properties of the substance to be measured is carried out using the above-illustrated method.

This device also gives a graphic display where each of the difference in the changing amounts in $F_2$ among the above-mentioned frequencies ($\Delta F_2$) and the difference in one half of the changing amounts of $F_1$, $F_2$ among the above-mentioned frequencies ($\Delta(F_1-F_2)/2$) is shown on the display of the computer 4.

EXAMPLES

An example of the preset invention will be mentioned as follows.

A quartz oscillator where resonance frequency was 27 MHz was dipped in a cell filled with a buffer (a biochemical buffer where main components therein were NaCl and KCl) and avidin, 30 mer b-DNA and 30 mer c-DNA were successively bonded thereto.

Figure 7:
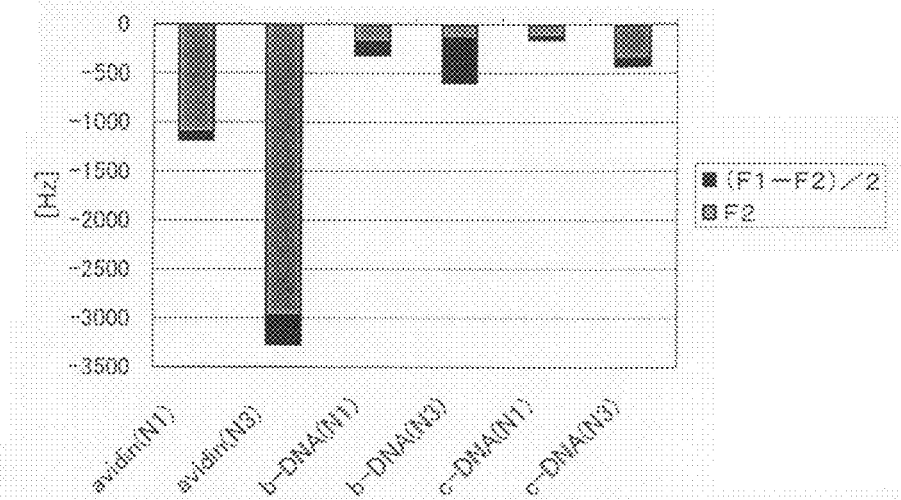
FIG. 7 is a graph which shows the measured result of an Example of the present invention.

At that time, frequencies $F_1$ and $F_2$ giving a half value of the conductance G (G/2) when the quartz oscillator was oscillated with a fundamental mode frequency (27 MHz) and a third overtone mode frequency (81 MHz) were used and changing amount of $\Delta F_2$ and changing amount of $\Delta(F_1-F_2)/2$ in each case was measured (FIG. 7).

When the value of $\Delta(F_1-F_2)/2$ greatly varies, it is noted from the above formula (6) that changes in viscosity and changes in viscoelasticity are great whereby it is found that changes in viscosity and changes in viscoelasticity are great when b-DNA is added.

Figure 8:
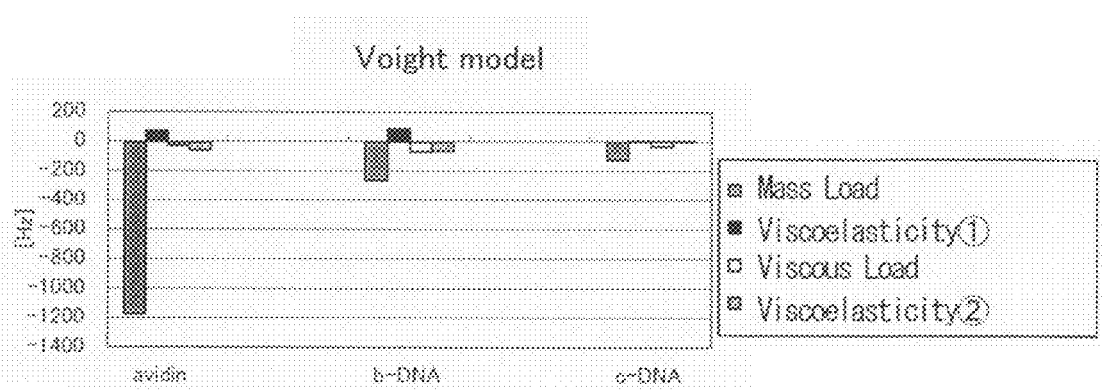
FIG. 8 is a graph which shows another measured result of said Example.
Figure 9:
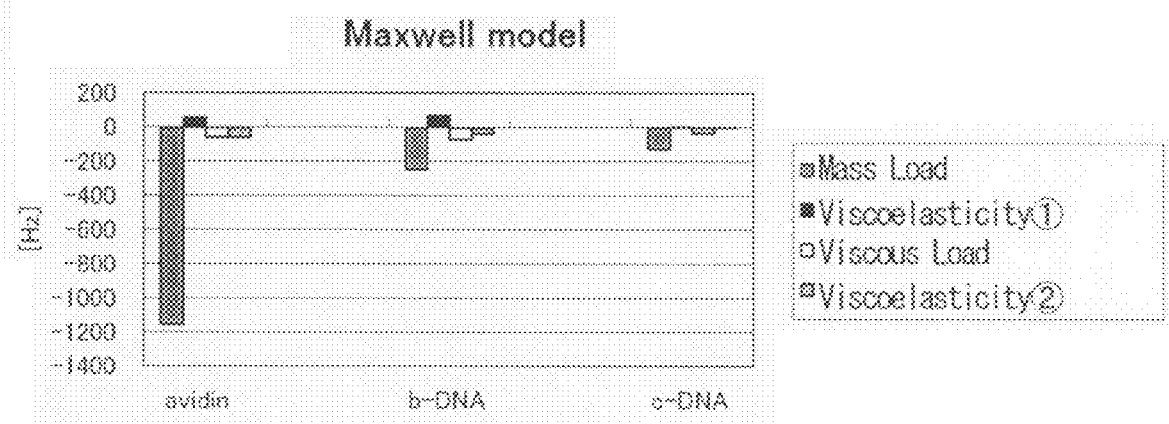
FIG. 9 is a graph which shows another measured result of said Example.

FIG. 8 is the result where the changing amount of $\Delta F_2$ and the changing amount of $\Delta(F_1-F_2)/2$ are applied to a Voight model and calculation is conducted on the basis of the above formulae (5) and (6) while FIG. 9 is the result of the calculation in a Maxwell model.

From those results, it is noted that changes in viscosity and changes in viscoelasticity which are properties of the additive is able to be measured separately from mass load. Further, when the case where avidin is bonded to the surface of the gold electrode of the quartz oscillator and the case where c-DNA is bonded to b-DNA are compared, there is no big change in viscoelasticity as compared with mass load but, when b-DNA is bonded to avidin, the rate of changing amount of frequency by viscoelasticity is great as compared with other bonds. Thus, it is noted that big changes in viscoelasticity is resulted.

INDUSTRIAL APPLICABILITY

The present invention is able to be utilized to measurement, etc. where interaction and antigen-antibody reaction of biomaterials such as DNA and protein are utilized.

The invention claimed is:

1. A method where property of a substance contacting to a quartz oscillator equipped with electrodes on both sides of a quartz plate is measured on the basis of the changes in frequency of the above quartz oscillator, characterized in that, the property of the above substance is measured using at least two mode frequencies among the n-th overtone mode frequencies of the quartz oscillator, wherein n=1, 3, 5, . . . , when voltage is applied between the above electrodes and using $F_{1@N1}$, $F_{2@N1}$ which are a set of frequencies $F_1$, $F_2$ measured by one n-th overtone mode frequency N1s, wherein $F_1<F_2$, giving one half of the maximum value of conductance near the resonant point by each frequency, and $F_{1@N1}$, $F_{2@N2}$ which are a set of frequencies $F_1$, $F_2$ measured by other n-th overtone mode frequencies, N2, wherein $F_1<F_2$ giving one half of the maximum value of conductance near the resonant point by each frequency, wherein the values of $\omega^2 \rho_2 \eta_2 h_1/\mu_1$ and C are determined from the measured value:

$$(\Delta F_{2@N1}/N1-\Delta F_{2@N2}/N2)/(\Delta(F_{1@N1}-F_{2@N1})/2N_1^{1/2}-\Delta(F_{1@N2}-F_{2@N2})/2N_2^{1/2})$$

wherein $\Delta F_{2@N1}/N1-\Delta F_{2@N2}/N2$ is expressed by the expression 9', and $\Delta(F_{1@N1}-F_{2@N1})/2N_1^{1/2}-\Delta(F_{1@N2}-F_{2@N2})/2N_2^{1/2})$ is expressed by the expression 10':

$$(N1\cdot(1+N1\cdot C)/(1+(N_1\cdot C)^2)-N2\cdot(1+N_2\cdot C)/(1+(N_2\cdot C)^2))\cdot\omega^2\rho_2\eta_2h_1/\mu_1 \quad \text{[Expression 9']}$$

wherein $\omega$ is angular frequency, $\eta_n$ is viscosity of the liquid, $\rho_n$ is density of the liquid, $h_n$ is film thickness and n is n-th layer, $$(-(N1)^{3/2}/(1+(N1\cdot C)^2)-(N2)^{3/2}/(1+(N2\cdot C)^2))\cdot\omega^2\Sigma_2\eta_2h_1/\mu_1 \quad \text{[Expression 10']}$$

wherein $\omega$ is angular frequency, $\eta_n$ is viscosity of the liquid, $\rho_n$ is density of the liquid, $h_n$ is film thickness and n is n-th layer, and after the values of $\omega^2 \rho_2 \eta_2 h_1/\mu_1$ and C are determined, the mass load, the viscoelasticity term 1, the viscous load and the viscoelasticity term 2 are obtained from the formula 7', formula 7'', formula 8' and formula 8'', respectively:

$$\text{the mass load}=\Delta F_{2N}/N-(1+C\cdot N)\cdot N\omega^2\rho_2\eta_2h_1/\mu_1(1+C^2N^2) \quad \text{[Formula 7']}$$

wherein $\omega$ is angular frequency, $\eta_n$ is viscosity of the liquid, $\rho_n$ is density of the liquid, $h_n$ is film thickness and n is n-th layer, $$\text{the viscoelasticity term }1=\Delta F_{2N}/N^2+\text{(the mass load)}/N, \quad \text{[Formula 7'']}$$

$$\text{the viscous load}=\Delta(F_{1N}-F_{2N})/2\cdot N_1^{1/2}+N^{3/2}\omega^2\rho_2\eta_2h_1/\mu_1\cdot(1+C^2N^2) \quad \text{[Formula 8']}$$

wherein $\omega$ is angular frequency, $\eta_n$ is viscosity of the liquid, $\rho_n$ is density of the liquid, $h_n$ is film thickness and n is n-th layer, $$\text{the viscoelasticity term }2=\Delta(F_{1N}-F_{2N})/2\cdot N^2+\text{(the viscous load)}\cdot N. \quad \text{[Formula 8'']}$$

2. A measuring device using the measuring method mentioned in claim 1, characterized in that, each of the difference in the changing amount of $F_2$ between the above frequencies and the difference in one half of the difference in $F_1$ and $F_2$ among the above frequencies is expressed by a graph generated on a computer screen.

3. A method where property of a substance contacting to a quartz oscillator equipped with electrodes on both sides of a quartz plate is measured on the basis of the changes in frequency of the above quartz oscillator, characterized in that, the property of the above substance is measured using at least two mode frequencies among the n-th overtone mode frequencies of the quartz oscillator, wherein n=1, 3, 5, . . . , when voltage is applied between the above electrodes and using $F_{1@N1}$, $F_{2@N1}$ which are a set of frequencies $F_1$, $F_2$ measured by one n-th overtone mode frequency, N1, wherein $F_1<F_2$, giving one half of the maximum value of conductance near the resonant point by each frequency, and $F_{1@N2}$, $F_{2@N2}$ which are a set of frequencies $F_1$, $F_2$ measured by other n-th overtone mode frequencies, N2, wherein $F_1<F_2$ giving one half of the maximum value of conductance near the resonant point by each frequency, wherein the values of $\omega^2 \rho_2 \eta_2 h_1/\mu_1$ and C are determined from the measured value:

$$(\Delta F_{2@N1}/N1-\Delta F_{2@N2}/N2)/(\Delta(F_{1@N1}-F_{2@N1})/2N_1^{1/2}-\Delta(F_{1@N2}-F_{2@N2})/2N_2^{1/2})$$

wherein $\Delta F_{2@N1}/N1-\Delta F_{2@N2}/N2$ is expressed by the expression 9', and
:$\Delta(F_{1@N1}-F_{2@N1})/2N_1^{1/2}-\Delta(F_{1@N2}-F_{2@N2})/2N_2^{1/2})$ is expressed by the expression 10':

$$(N1\cdot(1+N1\cdot C)/(1+(N_1\cdot C)^2)-N2\cdot(1+N_2\cdot C)/(1+(N_2\cdot C)^2))\cdot\omega^2\rho_2\eta_2h_1/\mu_1 \quad \text{[Expression 9']}$$

wherein $\omega$ is angular frequency, $\eta_n$ is viscosity of the liquid, $\rho_n$ is density of the liquid, $h_n$ is film thickness and n is n-th layer, $$(-(N1)^{3/2}/(1+(N1\cdot C)^2)-(N2)^{3/2}/(1+(N2\cdot C)^2))\cdot\omega^2\Sigma_2\eta_2h_1/\mu_1 \quad \text{[Expression 10']}$$

wherein $\omega$ is angular frequency, $\eta_n$ is viscosity of the liquid, $\rho_n$ is density of the liquid, $h_n$ is film thickness and n is n-th layer, and after the values of $\omega^2 \rho_2 \eta_2 h_1/\mu_1$ and C are determined, the n-th, mass load, the n-th viscoelasticity term 1, the n-th viscous load and the n-th viscoelasticity term 2, which are measured by the n-th overtone mode frequency, are obtained from the formula 7''', formula 7'''', formula 8''' and formula 8'''', respectively:

the $n$-th mass load$=\Delta F_{2N}-(1+C\cdot N)\cdot N^2\omega_1\rho_2\eta_2 h_1/\mu_1(1+C^2N^2)$ [Formula 7''']

wherein $\omega$ is angular frequency, $\eta_n$ is viscosity of the liquid, $\rho_n$ is density of the liquid, $h_n$ is film thickness and n is n-th layer, the n-th viscoelasticity term 1$=\Delta F_{2N}+$(the n-th mass load), [Formula 7'''']

the $n$-th viscous load$=\Delta(F_{1N}-F_{2N})/2+N^2\omega^2\rho_2\eta_2 h_1/\mu_1-(1+C^2N^2)$ [Formula 8''']

wherein $\omega$ is angular frequency, $\eta_n$ is viscosity of the liquid, $\rho_n$ is density of the liquid, $h_n$ is film thickness and n is n-th layer, the $n$-th viscoelasticity term 2$=\Delta(F_{1N}-F_{2N})/2+$(the $n$-th viscous load). [Formula 8'''']

\* \* \* \* \*